United States Patent [19]

Berg

[11] Patent Number: 5,106,460

[45] Date of Patent: Apr. 21, 1992

[54] SEPARATION OF 1,1,1-TRICHLOROETHANE FROM N-HEXANE BY EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 756,803

[22] Filed: Sep. 9, 1991

[51] Int. Cl.$^5$ .............. B01D 3/40; C07C 7/08; C07C 17/38
[52] U.S. Cl. ..................... 203/58; 203/60; 203/62; 203/63; 203/64; 570/262; 585/860; 585/864; 585/865; 585/866
[58] Field of Search ............ 203/60, 63, 64, 62, 203/58; 570/262; 585/800, 802, 860, 864, 865, 866

[56] References Cited

U.S. PATENT DOCUMENTS

| | | | |
|---|---|---|---|
| 3,113,079 | 12/1963 | Bergeron | 203/58 |
| 3,349,008 | 10/1967 | Vives | 570/262 |
| 3,658,657 | 4/1972 | Bursack et al. | 570/262 |
| 3,658,658 | 4/1972 | Bursack et al. | 570/262 |
| 3,989,601 | 11/1976 | Boozalis et al. | 570/262 |

FOREIGN PATENT DOCUMENTS

| | | | |
|---|---|---|---|
| 55-49325 | 4/1980 | Japan | 203/58 |
| 59-76026 | 4/1984 | Japan | 570/262 |

Primary Examiner—Wilbur Bascomb, Jr.

[57] ABSTRACT

1,1,1-Trichloroethane cannot be completely separated from n-hexane by conventional distillation or rectification because of the minimum boiling azeotrope. 1,1,1-Trichloroethane can be readily separated from n-hexane by extractive distillation. Typical effective agents are: methyl isoamyl ketone, amyl acetate and isobutanol.

1 Claim, No Drawings

SEPARATION OF 1,1,1-TRICHLOROETHANE FROM N-HEXANE BY EXTRACTIVE DISTILLATION

FIELD OF THE INVENTION

This invention relates to a method for separating 1,1,1-trichloroethane from n-hexane using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling compound. This usually requires that the extractive agent boil twenty Centigrade degrees or more above the lowest boiling component.

At the bottom of a continuous column, the less volatile components of the close boiling mixture and the extractive agent are continuously removed from the column. The usual methods of separation of these two components are the use of another rectification column, cooling and phase separation or solvent extraction.

1,1,1-Trichloroethane, B.P.+74.1° C. and n-hexane, B.P.=38.7° C. form a minimum boiling azeotrope boiling at 60° C. and containing 28.9% 1,1,1-trichloroethane. Extractive distillation would be an attractive method of separating 1,1,1-trichloroethane from n-hexane if agents can be found that (1) will enhance the relative volatility between 1,1,1-trichloroethane and n-hexane and (2) are easy to recover, that is, form no azeotrope with 1,1,1-trichloroethane or n-hexane and boil sufficiently above these two compounds to make separation by rectification possible with only a few theoretical plates.

The advantage of employing an effective extractive distillation agent is shown in Table 1, 1,1,1-Trichloroethane forms a minimum boiling azeotrope with n-hexane which possesses a relative volatility of 1.0 and cannot be completely separated by rectification. If extractive distillation is employed with an agent yielding a relative volatility of 2.5 or higher, rectification column of only seventeen actual plates will be required.

TABLE 1

| \multicolumn{4}{c}{Effect Of Relative Volatility On The Separation Of 1,1,1-Trichloroethane From n-Hexane At 99% Purity} | | | |
|---|---|---|---|
| Relative Volatility | Theoretical Plates | Actual Plates 75% Efficiency | Actual Plates 75% Eff., Min. Reflux |
| 1.2 | 52 | 70 | 91 |
| 1.5 | 23 | 31 | 41 |
| 2.0 | 13 | 17 | 22 |

TABLE 1-continued

| \multicolumn{4}{c}{Effect Of Relative Volatility On The Separation Of 1,1,1-Trichloroethane From n-Hexane At 99% Purity} | | | |
|---|---|---|---|
| Relative Volatility | Theoretical Plates | Actual Plates 75% Efficiency | Actual Plates 75% Eff., Min. Reflux |
| 2.5 | 10 | 13 | 17 |

OBJECTIVE OF THE INVENTION

The objects of this invention are to provide a process or method of extractive distillation that will enhance the relative volatility of 1,1,1-trichloroethane to n-hexane in their separation in a rectification column. It is a further object of this invention to identify organic compounds that are stable, can be separated from 1,1,1-trichloroethane or n-hexane by rectification with relatively few plates and can be recycled to the extractive distillation column with little decomposition.

SUMMARY OF THE INVENTION

The objects of this invention are provided by a process for the separation of 1,1,1-trichloroethane from n-hexane which entails the use of certain organic compounds as the agent in extractive distillation.

DETAILED DESCRIPTION OF THE INVENTION

I have discovered that certain organic compounds will effectively increase the relative volatility between 1,1,1-trichloroethane and n-hexane by rectification when employed as the agent in extractive distillation. Table 2 lists the compounds found to be effective. The data in Table 2 was obtained in a vapor-liquid equilibrium still. In every case, the starting mixture was the 1,1,1-trichloroethane - n-hexane azeotrope.

The compounds which are effective extractive distillation agents to separate 1,1,1-trichloroethane from n-hexane are n-propyl acetate, isopropyl acetate, n-butyl acetate, isobutyl acetate, n-amyl acetate, hexyl acetate, 2-ethyl hexyl acetate, 4-methyl pentyl acetate-2, isobornyl acetate, ethyl phenyl acetate, ethylene glycol ethyl ether acetate, 1-methoxy-2-propanol acetate, 2-methoxy ethyl acetate, ethyl propionate, ethyl butyrate, isobutyl butyrate, isobutyl isobutyrate, ethyl valerate, ethyl isovalerate, phenyl acetate, benzyl acetate, ethyl acetoacetate, methyl benzoate, ethyl benzoate, methyl salicylate, ethyl 3-ethoxy propionate, diethyl maleate, hexyl formate, ethylene glycol diacetate, isophorone, 4-methyl-2-pentanone, 3-hepatnone 2-heptanone, 5-methyl-2-hexanone, methyl isobutyl ketone, methyl isoamyl ketone, 2,6-dimethyl-4-heptanone, diisobutyl ketone, 2-octanone, isobutyl heptyl ketone, 3,3-dimethyl-2-butanone, 2-undecanone, 1-methyl-2-pyrrolidinone, n-butanol, isobutanol, 2-butanol, n-amyl alcohol, isoamyl alcohol, t-amyl alcohol, hexyl alcohol, heptyl alcohol, 2-octanol, isooctyl alcohol, n-decanol, 4-methyl-2-pentanol, tetrahydro furfuryl alcohol, diacetone alcohol, 1-methoxy-2-propanol, 3-methyl-1-butanol, 2-ethyl-1-butanol, ethylene glycol methyl ether and propylene carbonate.

TABLE 2

| Effective Agents For Separating n-Hexane From 1,1,1-Trichloroethane | |
|---|---|
| Compounds | Relative Volatility |
| n-Propyl acetate | 3.6 |

TABLE 2-continued

Effective Agents For Separating n-Hexane From 1,1,1-Trichloroethane

| Compounds | Relative Volatility |
|---|---|
| Isopropyl acetate | 2.7 |
| n-Butyl acetate | 1.9 |
| Isobutyl acetate | 1.9 |
| n-Amyl acetate | 1.45 |
| Hexyl acetate | 1.8 |
| 2-Ethyl hexyl acetate | 1.7 |
| 4-Methyl pentyl acetate-2 | 1.7 |
| Isobornyl acetate | 1.65 |
| Ethyl phenyl acetate | 1.95 |
| Ethylene glycol ethyl ether acetate | 1.4 |
| 1-Methoxy-2-propanol acetate | 2.0 |
| 2-Methoxy ethyl acetate | 2.5 |
| Ethyl propionate | 2.0 |
| Ethyl butyrate | 1.8 |
| Isobutyl butyrate | 1.65 |
| Isobutyl isobutyrate | 1.5 |
| Ethyl valerate | 1.85 |
| Ethyl isovalerate | 1.8 |
| Phenyl acetate | 2.1 |
| Benzyl acetate | 1.8 |
| Ethyl acetoacetate | 2.6 |
| Methyl benzoate | 2.2 |
| Ethyl benzoate | 1.95 |
| Methyl salicylate | 1.9 |
| Ethyl 3-ethoxy propionate | 2.1 |
| Diethyl maleate | 2.1 |
| Hexyl formate | 1.75 |
| Ethylene glycol diacetate | 2.4 |
| Isophorone | 2.1 |
| 4-Methyl-2-pentanone | 1.9 |
| 3-Heptanone | 1.85 |
| 2-Heptanone | 2.2 |
| 5-Methyl-2-hexanone | 2.0 |
| Methyl isobutyl ketone | 2.0 |
| 2,6-Dimethyl-4-heptanone | 1.7 |
| Diisobutyl ketone | 1.7 |
| 2-Octanone | 1.85 |
| Isobutyl heptyl ketone | 1.6 |
| 3,3-Dimethyl-2-butanone | 1.8 |
| 2-Undecanone | 1.85 |
| 1-Methyl-2-pyrrolidinone | 3.9 |
| n-Butanol | 1.8 |
| Isobutanol | 3.4 |
| 2-Butanol | 1.9 |
| n-Amyl alcohol | 1.85 |
| Isoamyl alcohol | 1.5 |
| t-Amyl alcohol | 3.3 |
| Hexyl alcohol | 1.7 |
| Heptyl alcohol | 1.95 |
| 2-Octanol | 1.35 |
| Isooctyl alcohol | 2.2 |
| n-Decanol | 1.5 |
| 4-Methyl-2-pentanol | 1.9 |
| Tetrahydro furfuryl alcohol | 2.5 |
| Diacetone alcohol | 2.3 |
| 1-Methoxy-2-propanol | 2.0 |
| 3-Methyl-1-butanol | 1.8 |
| 2-Ethyl-1-butanol | 1.65 |
| Ethylene glycol methyl ether | 3.2 |
| Propylene carbonate | 2.0 |
| Methyl isoamyl ketone | 2.0 |

TABLE 3

Data From Run Made In Rectification Column

| Agent | Column | Time hrs. | Weight % n-Hexane | Weight % C₂H₃Cl₃ | Relative Volatility |
|---|---|---|---|---|---|
| Methyl isoamyl ketone | Overhead | 1 | 94.9 | 5.1 | 1.5 |
| | Bottoms | | 50.7 | 49.3 | |
| Methyl isoamyl ketone | Overhead | 2 | 82.2 | 17.8 | 1.95 |
| | Bottoms | | 3.3 | 96.7 | |

One of the agents, methyl isoamyl ketone, whose relative volatility had been determined in the vapor-liquid equilibrium still, was then evaluated in a glass perforated plate rectification column possessing 7.3 theoretical plates and the results listed in Table 3. Methyl isoamyl ketone gave a relative volatility of 1.95 after two hours of operation.

THE USEFULNESS OF THE INVENTION

The usefulness or utility of this invention can be demonstrated by referring to the data presented in Tables 1, 2 and 3. All of the successful agents show that 1,1,1-trichloroethane can be separated from n-hexane by means of extractive distillation in a rectification column and that the ease of separation as measured by relative volatility is considerable.

WORKING EXAMPLES

Example 1

Sixty grams of the 1,1,1-trichloroethane - n-hexane azeotrope and 30 grams of methyl isoamyl ketone were charged to a vapor-liquid equilibrium still and refluxed for five hours. Analysis indicated a vapor composition of 53.6% n-hexane, 46.4% 1,1,1-trichloroethane; a liquid composition of 36.1% n-hexane, 63.9% 1,1,1-trichloroethane which is a relative volatility of 2.0.

Example 2

A solution comprising 300 grams of the 1,1,1-trichloroethane - n-hexane azeotrope was placed in the stillpot of a 7.3 theoretical plate glass perforated plate rectification column. When refluxing began an extractive agents comprising methyl isoamyl ketone was pumped into the column at a rate of 15 ml/min. The temperature of the extractive agent as it entered the column was 85° C. After establishing that the feed rate of the extractive agent, the heat input to the 1,1,1-trichlorethane - n-hexane in the stillpot was adjusted to give a total reflux rate of 40 ml/min. After two hours of operation, the overhead and bottoms samples were collected and analysed. The overhead analysis was 82.2% n-hexane, 17.8% 1,1,1-trichloroethane and the bottoms analysis was 3.3% n-hexane, 96.7% 1,1,1-trichloroethane. This gives as average relative volatility of 1.95 for each theoretical plate. This data is presented in Table 3.

I claim:

1. A method for recovering 1,1,1-trichloroethane from a mixture of 1,1,1-trichloroethane and n-hexane which comprises distilling a mixture of 1,1,1-trichloroethane and n-hexane in the presence of about one part of an extractive agent per part of 1,1,1-trichloroethane - n-hexane mixture, recovering the n-hexane as overhead product and obtaining the 1,1,1-trichloroethane and the extractive agent from the stillpot, wherein said extractive agent consists of one material selected from the group consisting of n-propyl acetate, isopropyl acetate, n-butyl acetate, isobutyl acetate, n-amyl acetate, hexyl acetate, 2, -ethyl hexyl acetate, 4-methyl pentyl acetate-2, isobornyl acetate, ethyl phenyl acetate, ethylene glycol ethyl ether acetate, 1-methoxy-2-propanol acetate, 2-methoxy ethyl acetate, ethyl propionate, ethyl butyrate, isobutyl butyrate, isobutyl isobutyrate, ethyl valerate, ethyl isovalerate, phenyl acetate, benzyl acetate, ethyl acetoacetate, methyl benzoate, ethyl benzoate, methyl salicylate, ethyl 3-ethoxy propionate, diethyl maleate, hexyl formate, ethylene glycol diacetate, isophorone, 4-methyl-2-pentanone, 3-heptanone, 2-heptanone, 5-methyl-2-hexanone, methyl isobutyl ketone, methyl isoamyl ketone, 2,6-dimethyl-4heptanone, diisobutyl ketone, 2-octanone, isobutyl heptyl ketone, 3,3-dimethyl-2-butanone, 2-undecanone 1-methyl-2-pyrrolidinone, n-butanol, isobutanol, 2-butanol, n-amyl alcohol, isoamyl alcohol, t-amyl alcohol, hexyl alcohol, heptyl alcohol, 2-octanol, isooctyl alcohol, n-decanol, 4-methyl-2-pentanol, tetrahydro furfuryl alcohol, diacetone alcohol, 1-methoxy-2-propanol, 3-methyl-1-butanol, 2-ethyl-1-butanol, ethylene glycol methyl ether and propylene carbonate.

* * * * *